United States Patent [19]

Beckstein

[11] Patent Number: 4,676,651

[45] Date of Patent: Jun. 30, 1987

[54] METHOD AND APPARATUS FOR CONTROLLING THE DYE RECEPTIVITY OF TEXTILES

[75] Inventor: Hellmut Beckstein, Bad Abbach, Fed. Rep. of Germany

[73] Assignee: Mahlo GmbH+Co. KG., Donau, Fed. Rep. of Germany

[21] Appl. No.: 603,604

[22] Filed: Apr. 25, 1984

[30] Foreign Application Priority Data

May 4, 1983 [DE] Fed. Rep. of Germany ....... 3316172

[51] Int. Cl.$^4$ ............................................ G01N 21/84
[52] U.S. Cl. ..................... 356/429; 356/433
[58] Field of Search ................................. 356/429, 433

[56] References Cited

FOREIGN PATENT DOCUMENTS 1938083 11/1972 Fed. Rep. of Germany .
2655973 12/1982 Fed. Rep. of Germany .

*Primary Examiner*—Bernard D. Pianalto
*Attorney, Agent, or Firm*—W. G. Fasse; D. H. Kane, Jr.

[57] ABSTRACT

For controlling the dye receptivity or color absorption capacity of a running web of textile goods, a monitoring method by means of electromagnetic waves penetrating through the web of goods is used (FIG. 2).

5 Claims, 2 Drawing Figures

METHOD AND APPARATUS FOR CONTROLLING THE DYE RECEPTIVITY OF TEXTILES

DESCRIPTION OF THE PRIOR ART

A large problem, which is decisive for the loss of quality, in the dyeing of textiles, is the non-uniform color distribution over the width and length of the pieces to be dyed. Color or dye variations, so-called color or dye run-offs, between the middle of the web and the edge zones are not rare. Similarly, such variations also frequently occur between the beginning and end of a textile web. In the manufacture of ready-to-wear clothing made of such colored articles, such color deviations then arise as unacceptable color variations, for instance, within a piece of clothing.

Dyeing errors of this type can have various causes. Depending on the dyeing method employed, machine or technical errors, operator's errors, and especially non-uniformities in the raw goods are possible. One cause for color or dye run-offs is the application of varying amounts of dye liquor onto the textile goods arising for instance, due to a non-uniform squeezing-out of the goods. Thus, there are devices known which allow controlling the amount of water distributed across the width of the goods, for example, with the aid of moisture measuring devices according to the microwave-absorption method (German Patent (DE-PS) No. 2,655,973). In order to monitor the color uniformity, colorimetric measuring devices have also been developed, which allow the colors to be objectively measured directly on the running web of goods, but of course, only after the drying of the dye.

The measurement of the distribution of the watery color dye liquor and the possible regulation or control of this distribution however takes into consideration only one of the many causes for the color non-uniformities, and at that—as is shown by the experiences of dyers—not even the decisive cause. On the other hand, the raw goods themselves frequently include peculiarities, which cause a varying dye liquor absorption. Such peculiarities include, for example, a non-uniform weight per surface area, but also above all, non-uniform dye absorption characteristics, caused, for example, by fluctuations in the structure of the textile, by the fiber roughness, by the size and distribution of the capillaries between the fibers, by the hygroscopic behavior dependent thereon and the like.

It is therefore very important for the dyer to know the color absorption or dye receptivity characteristics of a supplied undyed piece, already before the dyeing, so that especially non-uniform batches will, from the start, not be provided for a single color dyeing, for instance. Such pieces may on the other hand, be useful for printing or for other purposes in which color run-offs do not play an important roll.

OBJECTS OF THE INVENTION

It is therefore the object of the invention to provide a method and apparatus for the control of textiles, by means of which rejects of the textile goods due to color variations, may be avoided without damage to the textiles. This object is achieved by the features of the claims.

SUMMARY OF THE INVENTION

The invention is based on the recognition that a relation exists between the dye receptivity of textiles and the permeability thereof. Varying permeabilities of a web of goods with respect to light, cause respective non-uniform color or dye distributions, whereby such permeability variations are not necessarily based on variations in the weight per surface area. Rather, more often such permeability variations are caused by differences in the structure of the textiles, which are apparent in the number, type, shape and size of the interstitial spaces or capillaries between the fibers and on the spaces between the threads, in the appearance of the surface of the yarns, and similar mechanical textile characteristics. The causes for such differences may be found in the material production, e.g., weaving or knitting, as well as already in the yarns themselves which are used to make the fabric.

For the purpose of controlling, according to the invention, the dyeability of textiles, light is applied to the textiles at one or several locations on the web at the edges or the center thereof, by means of one or several measuring heads traversing across the web, or by means of band-shaped measuring systems which reach across the entire width. The amount or quantity of the energies passing through the textile is measured with the aid of appropriate receivers. This measuring may be achieved with receivers for light intensity or amplitudes. The received signals measured at the various locations of the web are compared with each other in a comparator arrangement; a computer can calculate the percentile deviations; a printer or a writing-recoder can record the uniformity or non-uniformity which includes said deviations.

DESCRIPTION OF THE PRIOR ART

A monitoring method for textile goods by means of light waves penetrating through the textile is known as such from German Patent Publication (DE-PS) No. 1,938,083. However, this known method is used for monitoring the textile goods for visible localized flaws, such as holes, missing warp threads, missing meshes, missing woof threads, oil spots, bound-in extraneous bodies, loops, etc. In contrast thereto, invisible structure variations extending over large surfaces are determined according to the invention.

In the following it will be described by way of an example, how such a measuring arrangement may be constructed.

BRIEF FIGURE DESCRIPTION

In order that the invention may be clearly understood, it will now be described, by way of example, with reference to the accompanying drawings, wherein.

Figure 1:
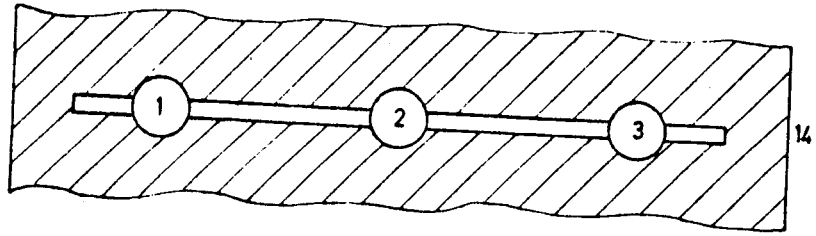
FIG. 1 shows a top view.
Figure 2:
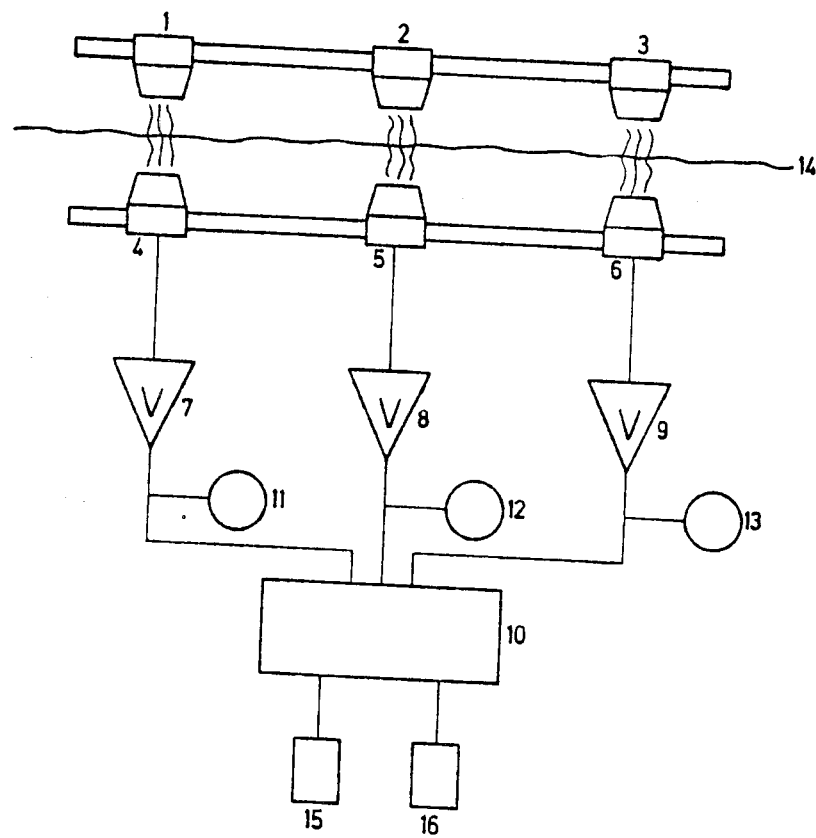
FIG. 2 shows schematically a sectional view of the measuring arrangement for measuring the dye receptivity of characteristics of the goods.

DETAILED DESCRIPTION OF PREFERRED EXAMPLE EMBODIMENTS AND OF THE BEST MODE OF THE INVENTION

Light is produced by the transmitters 1 to 3 and is radiated onto the web of goods 14. The receivers 4 to 6 may be light quantity or intensity measuring sensors, which convert the energies passing through the textile into electric signals. The received energies are compared to their respective transmitted energies. The damping is determined by this comparing. The damping is a measure of the permeability of the goods being tested. Additionally, the dampings of the three sections (1-4, 2-5, and 3-6) are compared with each other in a circuit 10, in order to determine non-uniformities in the permeability. Finally, the permeability of the test goods is indicated at three locations (middle and both edges) by the indicators 11, 12, and 13. Simultaneously, the permeability may be printed at 15 or it may be written at 16. The printer or writer outputs are for example passed on with the textile pieces as data for the dyeing. 7, 8, and 9 are amplifiers.

For achieving the purpose of the invention only relative measured values, or the comparison relative to a prescribed standard over the length of the web, are necessary. Therefore, only sufficiently similar measuring arrangements are required, not however, reproduceable absolute, measured values. The choice of the measuring medium to use depends upon the conditions and characteristics of the textile goods to be tested. However such conditions and characteristics may vary considerably. Thus, very open or loose textiles are tested with light as a medium.

Due to the required uniformity of the characteristics of the individual measuring sections, it may be recommendable under certain circumstances to use a single measuring device, which is moved across the web for producing a non-interrupted profile of the permeability ratios or characteristics. It is also conceivable to use two or more measuring devices moving symmetrically relative to the middle of the web, thereby the signals from these masuring devices are compared constantly with each other in pairs.

Although the invention has been described with reference to specific example embodiments, it will be appreciated, that it is intended to cover all modifications and equivalents within the scope of the appended claims.

What is claimed is:

1. A method for preparing a record of the dye receptivity characteristics of an undyed web of textile for the subsequent use by the dyer, comprising the following steps:
   (a) running said web of textile through a measuring station including magnetic wave transmitter means and magnetic wave receiver means,
   (b) transmitting magnetic wave energy from one side of said web through said web of textile,
   (c) receiving magnetic wave energy that has passed through said web on the other side of said web,
   (d) comparing the transmitted energy with the received energy for determining a damping caused by the web of textile, said damping providing a measure of the permeability of the web of textile,
   (e) comparing dampings measured at different locations in said web of textile with each other for determining non-uniformities in said permeability, and
   (f) recording said non-uniformities in said permeability which constitute a measure of said dye receptivity to form said record.

2. The method of claim 1, comprising using light energy as said magnetic wave energy.

3. An apparatus for producing a record of the dye receptivity characteristics of an undyed web of textile for the subsequent use by the dyer, said web running through a measuring station, comprising transmitter means located for transmitting magnetic wave energy from one side of said web through said web of textile, receiver means located for receiving magnetic wave energy that has passed through said web, means for comparing the transmitted energy with the received energy for determining a damping providing a measure of the permeability of the web of textile, means for comparing dampings measured at different locations in said web of textile with each other for determining non-uniformities in said permeability, and means for recording said non-uniformities in said permeability which constitute a measure of said dye receptivity to form said record.

4. The apparatus of claim 3, wherein said transmitter means comprise at least one transmitter on one side of said web of textile and wherein said receiver means comprise at least one receiver located opposite the transmitter on the other side of said web of textile, said transmitter (1, 2, 3) and said receiver (4, 5, 6) being movable perpendicularly to the web of textile (14).

5. The apparatus of claim 3, wherein two or more even numbered transmitters/receivers are movable back and forth symmetrically relative to the middle of the web.

* * * * *

UNITED STATES PATENT AND TRADEMARK OFFICE
CERTIFICATE OF CORRECTION

PATENT NO. : 4,676,651

DATED : June 30, 1987

INVENTOR(S) : Hellmut Beckstein

It is certified that error appears in the above-identified patent and that said Letters Patent is hereby corrected as shown below:

On the title page Assignee should read,

--[73] Assignee: Mahlo GmbH + Co. KG.,     Saal/Donau, Fed. Rep. of Germany--.

Signed and Sealed this

Sixteenth Day of February, 1988

Attest:

DONALD J. QUIGG

*Attesting Officer*     *Commissioner of Patents and Trademarks*